(12) United States Patent
Cherry et al.

(10) Patent No.: US 6,281,801 B1
(45) Date of Patent: Aug. 28, 2001

(54) SYSTEM AND METHOD FOR MONITORING WATER CONTENT OR OTHER DIELECTRIC INFLUENCES IN A MEDIUM

(75) Inventors: Robert S. Cherry, Idaho Falls; Allen A. Anderson, Firth, both of ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/090,675

(22) Filed: Jun. 3, 1998

Related U.S. Application Data

(60) Provisional application No. 60/048,598, filed on Jun. 4, 1997.

(51) Int. Cl.[7] ..................................................... G08B 21/00
(52) U.S. Cl. ......................... 340/605; 340/604; 324/643; 73/61.41
(58) Field of Search ..................................... 340/605, 604; 324/643; 73/61.41, 73

(56) References Cited

U.S. PATENT DOCUMENTS

| | | | |
|---|---|---|---|
| 4,918,375 | * | 4/1990 | Malicki et al. ....................... 324/642 |
| 5,073,756 | * | 12/1991 | Brandelik .............................. 324/643 |
| 5,442,293 | * | 8/1995 | Lange .................................... 324/332 |
| 5,999,121 | * | 12/1999 | Salonen ................................. 342/351 |

* cited by examiner

Primary Examiner—Edward Lefkowitz
(74) Attorney, Agent, or Firm—Workman Nydegger & Seeley

(57) ABSTRACT

A sensor system is provided that measures water content or other detectable properties in a medium along the entire length of the sensor at any point in time. The sensor system includes an electromagnetic signal generator and a transmission line disposed in a medium to be monitored. Alternatively, the transmission line can be configured for movement across a medium to be monitored, or the transmission line can be fixed relative to a moving medium being monitored. A signal is transmitted along the transmission line at predetermined frequencies, and the signal is returned back along the transmission line and/or into an optional receive line in proximity to the transmission line. The returned signal is processed to generate a one-dimensional data output profile that is a function of a detectable property of the medium. The data output profile can be mapped onto a physical system to generate a two-dimensional or three-dimensional profile if desired. The sensor system is useful in a variety of different applications such as agriculture, horticulture, biofiltration systems for industrial offgases, leak detection in landfills or drum storage facilities at buried waste sites, and in many other applications.

71 Claims, 3 Drawing Sheets

SYSTEM AND METHOD FOR MONITORING WATER CONTENT OR OTHER DIELECTRIC INFLUENCES IN A MEDIUM

RELATED APPLICATION

This application claims priority from provisional application Ser. No. 60/048,598 filed Jun. 4, 1997.

CONTRACTUAL ORIGIN OF THE INVENTION

The United States Government has rights in this invention pursuant to Contract No. DE-AC07-94ID13223 between Lockheed Martin Idaho Technologies Company and The United States Department of Energy.

BACKGROUND OF THE INVENTION

1. Field of the Invention

The present invention relates to techniques for deriving and evaluating information within a medium. More particularly, the present invention relates to a system and method for monitoring water content or other dielectric influences in a medium such as a bed of solids.

2. Relevant Technology

Many techniques have been developed for monitoring water content or other dielectric influences in various materials and locations. Some of these techniques for measuring local water content are based on resistance, capacitance, or impedance. One technique is known as time domain reflectometry (TDR), which measures the average water content over a relatively short probe length. In TDR, two conducting probes are disposed in a medium to be measured such as soil or air. One of the probes carries a signal, while the other probe acts as a ground. A short pulse is transmitted down one of the probes by a signal generating device. The pulse is reflected off the end of the transmit probe and goes back along the same probe. When more water is present in the medium, the signal will travel more slowly, and by determining the travel time of the pulse down the probe and back to a measuring instrument, the water content averaged over the length of the probe is measured. A problem that occurs with TDR is that the water in the medium also absorbs energy from the pulse, thereby making the pulse weaker. This in turn adversely affects the accuracy of the measurement, resulting in limits on the length over which the water content can be measured.

A dielectric imaging system is disclosed in U.S. Pat. No. 5,363,050 to Guo et al., in which a transmitter transmits microwaves toward a target, and the target scatters the microwaves. The scattered waves are received by an antenna and are converted into suitable data for application to a digital computer. The computer processes the data using either a scattering matrix algorithm or a Fourier transform algorithm. The computer then generates data representative of a three-dimensional profile of dielectric permittivity which can be displayed on a display device. A problem with this system, however, is that the targeted sample for measurement must fit inside of the transmitter/antenna configuration, limiting the size of the measured sample.

In U.S. Pat. No. 4,755,944 to Glass, a method for obtaining dielectric constant and conductivity information on a subsoil structure is disclosed. In the method, at least two boreholes are created in a subsoil area to be examined, with at least one electromagnetic radiation transmitter placed in one borehole and at least one receiver placed in a second borehole, both at various locations along the boreholes. The transmitter produces a continuous constant signal which traverses the plane between the transmitter and the receiver. After measuring simultaneously both the amplitude and phase of the received electromagnetic signal, the signal information is processed using a linear approximation algorithm. Upon comparison of the processed data with standard data for nearby geological formations, it is possible to accurately determine both the dielectric constant and the conductivity of the subsoil measured. A problem with this method is that it requires measurements to be taken at multiple places along the boreholes, resulting in a labor intensive data processing method and a large set of data that must be processed to obtain the desired measurements.

A commercially available technology exists for monitoring the internal dielectric properties of transmission lines and other electrical systems. Known as network analyzers, these instruments supply electromagnetic signals at a variety of frequencies into a transmission line system. By analyzing the amount of signal that is reflected back into the instrument or that passes through the system to be returned to the instrument through a different transmission line, a network analyzer can determine the location of defects in the transmission line. The analysis that is done is some form of an inverse fast Fourier transform. Network analyzers designed to monitor the performance and integrity of such things as analyzers are designed to monitor the performance and integrity of such things as antenna wiring and undersea telephone cables where physical inspection may be difficult. However, they do not by themselves provide information about the medium around the transmission lines.

One area in which monitoring of water content is important is in biofiltering systems to decontaminate air streams. Certain biofilters work by passing a continuous flow of contaminated air through a filtering material such as compost or other organic material containing bacteria. This filtering material works only to the extent that a certain level of moisture is maintained. In the past, dielectric sensors have been placed into biofilters to give a "point" reading of moisture at a particular location. Alternatively, the total weight of the bed can be measure. The difficulty with these approaches is that water is lost in a greater amount near the influent of the air and to a lesser amount at the effluent. Thus, data related to the distribution of water composition in a biofilter, which is important to know for many types of biofilters, is not accurately obtained.

Accordingly, there is a need for an improved system and method for monitoring water content or other detectable properties that overcomes or avoids the above problems.

SUMMARY AND OBJECTS OF THE INVENTION

The present invention is directed to a sensor system and method for monitoring detectable properties such as water content in a medium. The sensor system includes a means for generating and transmitting an electromagnetic signal, such as a signal generator. A signal-leaking transmission line is operatively connected to the generating means and is disposed in a medium to be monitored. An optional receive line can be disposed in the medium in proximity to the transmission line. Alternatively, the transmission and receive lines can be configured for movement across a medium to be monitored or can be fixed relative to a moving medium being monitored.

A means for processing and analyzing data received from the transmission line and/or receive line if used is also provided such as a digital signal processor. In addition, an output device for displaying a profile generated by the processing means can also be employed. The processing means generates the profile of the detectable property of the medium by using an inverse fast Fourier transform algorithm to convert data from the frequency domain to the time domain.

In one embodiment, the transmission line and receive line are slotted coaxial cables. The slotted coaxial cables can be disposed in the medium substantially parallel to one another or in other configurations as desired.

In a method of operating the system of the invention, an electromagnetic signal such as a microwave signal is transmitted from a signal generator along the transmission line disposed in the medium, and is reflected back along the transmission line and/or into the receive line, if present. The electromagnetic signal can be transmitted as a swept or stepped frequency signal of electromagnetic energy, or a pulse of electromagnetic energy may alternatively be used. The returned signal is processed to generate a one-dimensional profile that is a function of the detectable property of the medium at a measured location. A selected amount of the profile can then be displayed on the output device. The displayed profile can represent changes in the medium such as moisture content, chemical composition, temperature, percent solids or liquid, salinity, physical integrity, structural integrity, etc.

The resolution of the profile and the maximum length over which the profile can be measured are determined by the number of different frequencies used and the spacing between them. Through manipulation of these operating variables and by applying various known windowing techniques, the profile of properties can be measured over a limited section of the entire cable in greater detail, but at the expense of no information in other parts of the cable. Greater detail could be obtained over the entire cable at the expense of the use of greater number of frequencies which requires more time to collect and to process the correspondingly greater amount of data. By changing operating conditions, a relatively coarse but fast scan of the entire profile can be done to identify areas of particular interest which are then subjected to more detailed local analysis.

In addition, the generated one-dimensional profile, which relates to distance or time measurement along the transmission line, can be used in a further data processing step to construct a two-dimensional or three-dimensional output for the physical system that is being measured. This can be accomplished by physically laying out the transmission line in a two-dimensional or three-dimensional pattern and then doing the appropriate mapping and interpolation of data.

The sensor system of the present invention is useful in a variety of different applications. The sensor system can be used in agriculture for determining local irrigation requirements including precision irrigation of field crops, in biofiltration systems for industrial offgases to indicate improper watering of the biofilter bed, and in detecting leaks from landfill areas or drum storage facilities at buried waste sites. In addition, the water profile data produced by the sensor system can also be used in monitoring composting operations, maintaining lawns or golf course greens, monitoring grain and potato storage facilities, monitoring water infiltration into cracked concrete structures, and in many other applications.

Accordingly, a principle object of the present invention is to provide a sensor system that can monitor various detectable properties in a medium.

Another object of the invention is to provide a method for monitoring various detectable properties in a medium in a variety of different applications.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

Figure 1:
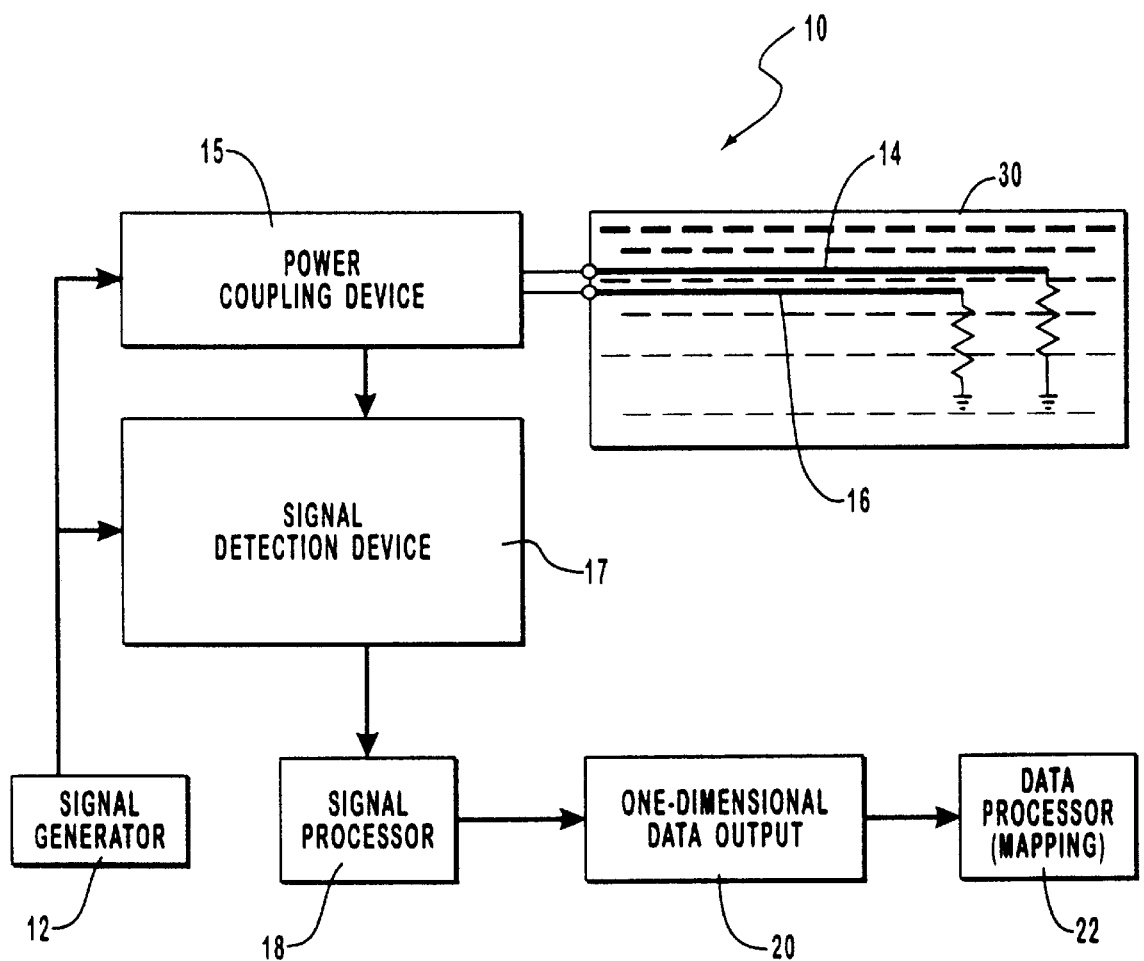
FIG. 1 is schematic block diagram of the sensor system according to one embodiment of the present invention.

The present invention is directed to a sensor system and method for measuring the profile of water content or other detectable properties in a medium along the entire length of the sensor at any point in time or continuously in time. The sensor system includes a signal leaking transmission line or a pair of such transmission lines, such as a small diameter cable or cables, which are installed or located in an area to be monitored and are coupled to a dedicated set of electronic instruments. A signal processor analyzes a low power electromagnetic signal propagated along the transmission line to determine the detectable properties of the medium as a function of distance down the transmission line. The electronic instruments can be multiplexed between several cables or removed entirely when not needed.

The sensor system of the present invention detects changes in the electrical or electromagnetic properties of the medium that is being monitored which allows inferences to be made about changes in water content or other detectable physical and chemical properties of the medium. The sensor system allows continuous measurement of water content or other detectable properties at all points along the transmission line(s). In addition, the sensor system can be applied to measure any physical variable, such as temperature or density in beds of compressible solids, which affect a material's dielectric constant or other electromagnetic properties.

The sensor system of the invention is sensitive in varying degrees to changes in the medium that will affect the electrical permittivity or magnetic permeability of the medium. The sensor system may be used to monitor either gradual or abrupt discontinuities with respect to both time and space which may affect the intrinsic impedance of the medium or cause scattering or reflections of the electromagnetic energy applied. This may include fracture/fatigue formation, intrusion, and changes in the chemical and/or structural composition. The types of media compatible with the sensor system can include an extremely broad range of materials, with careful selection in monitoring applications and adaptation of the system. Compatible types of media include air and other gases, solids, or particulate matter, liquids and mixtures of these phases. For example, soils, concrete, metals, plastics, ceramics, water, and other inorganic or organic liquids can be monitored by the sensor system.

The sensor system detects changes in the propagation and/or the reflection of electromagnetic (EM) energy in the medium. Electromagnetic energy consists of both electric and magnetic components. Therefore, any change in the medium which affects either of these components will affect the propagation characteristics through the medium. Characteristics of the medium which will affect the propagation and reflection of energy include the electrical conductivity and permittivity, as well as the magnetic permeability of the material. Energy propagation and reflection will also be affected by the continuous nature in the chemical and molecular structure of the medium, as well as the electrical and magnetic properties of the medium material. Therefore, the present sensor system is designed to detect changes in the molecular structure and composition of the medium material.

Examples of possible material changes that can be detected by the sensor system include the infiltration of water and other inorganic/organic species into a medium, the polymerization of plastics, the displacement of air as a porous material is compressed, the fluctuation of temperature in a medium, the fracturing of the medium which allows air to replace a portion of a solid medium, and the replacement of a medium with a material of different properties. Objects or other materials having a relatively high electrical conductivity and/or magnetic permeability that move into or out of proximity with the medium being analyzed may also alter the propagation of EN energy in the medium. Therefore, the sensor system is also designed to detect either the removal or insertion of characteristically different materials in regions surrounding the medium of interest.

The sensor system of the invention may be configured and tailored for each application in order to achieve the sensitivity required to monitor the complex interactions described above. The sensor system can be configured to monitor not only changes in permittivity or permeability, but can be used in the detection of internal and external anomalies such as fractures, fatigue, and temperature in the medium.

Referring to FIG. 1, a schematic block diagram of sensor system 10 according to one embodiment of the present invention is depicted. The sensor system 10 includes a means for generating an electromagnetic signal, such as a signal generator 12 shown in FIG. 1. The signal generator 12 can be employed to produce a swept or stepped frequency signal from the audio to the microwave range, or a pulse signal may be produced. One example of a suitable signal generator is a microwave sweep oscillator. The signal generator 12 is operatively attached to a transmit line 14 through a power coupling device 15 that provides circuitry for signal power coupling and frequency multiplexing.

The transmit line 14 and an optional receive line 16 in proximity thereto are disposed in a medium 30 to be measured. The transmit line 14 and receive line 16 are buried in or located on the medium to be monitored. Alternatively, transmit line 14 and receive line 16 can be configured for movement across a medium to be measured or can be fixed relative to a moving medium. The power coupling device 15 is operatively connected to receive line 16 and a signal detection device 17. The signal detection device 17 is provided with a means for measuring the strength of the returned signal as a function of frequency, such as active and passive solid state technology known to those skilled in the art.

In one embodiment, the transmit line 14 and receive line 16 are coaxial cables with a slotted shield, which are deployed side-by-side. In general, the cables are transmission lines or waveguides designed to leak or radiate a portion of the EM energy they carry into the surrounding environments. As shown in the embodiment of FIG. 1, the cables can be deployed substantially parallel to one another, although other configurations may be used as described in more detail below. The slotted coaxial cables preferably include a corrugated copper shield in which portions of the high spots of the corrugation have been removed along the length of the cable to form holes to provide leakage of a signal. The slotted coaxial cables act as paired transmitter/receiver of the signal generated, and are designed to radiate and/or receive EM energy along the lengths thereof.

The slotted coaxial cables can be a few meters in length up to hundreds or even thousands of meters long, yet only one set of electronics is needed to monitor the entire length. The pair of slotted coaxial cables can be placed a few inches apart from each other up to a few feet apart in the sensor system of the invention. For example, the cables can be placed about one inch apart up to about 6 ft apart, depending on the sensor system application. The slotted shield on the cables allow the loss or pickup of microwave radiation uniformly along the length of the cables. This capability is used to transfer EM energy from one cable, through the material in which the cables are buried, and into the other cable. The amount of EM energy transferred through material is affected by the local water content or other detectable property and is carefully measured across a wide frequency range.

The sensor system 10 also includes a means for processing and analyzing data such as a signal processor 18 operatively attached to signal detection device 17. The signal processor 18 is preferably a digital signal processor, which provides control of the system and processing of data by analyzing the received signal. The amount of energy transferred between the transmit and receive lines is affected by the local properties in the medium and is measured across a wide frequency range by the signal processor which analyzes the ratio of signal return to signal transmitted as a function of frequency. Using an inverse fast Fourier transform algorithm, the measured data is converted from the frequency domain into the time domain. This time domain signal can then be related to distance along the transmission line. A one-dimensional data output 20 operatively connected to signal processor 18 can be displayed using a CRT to provide an output for the processed data in a readily understood format. The one-dimensional data output 20 can also provide external feedback control. Various output formats can be utilized, depending on the particular use to which the sensor system is applied, in order to provide a user-friendly output for interpretation of the data by the instrument operator.

The processing means can also include an optional data processor 22 that is operatively connected to one-dimensional data output 20. The data processor 22 can be employed for mapping the one-dimensional data onto a physical system to generate information across a two-dimensional area or three-dimensional volume. As discussed in greater detail below, by doing the appropriate interpolation, a two-dimensional or three-dimensional profile of the monitored area can be generated.

In another embodiment of the sensor system of the invention, transmit line 14 is utilized without receive line 16. In this embodiment, the signal is transmitted and returned back along the same line 14. The electronic components used in this embodiment to transmit and analyze the signal are the same as discussed above for the embodiment of FIG. 1.

In a further embodiment, a network analyzer can be used to provide the electronic components for transmitting and analyzing the signal in the sensor system of the invention. A network analyzer is a commercially available electronic instrument, which is used for measuring signal transmission and reflection in materials such as in cable and antenna systems or in other custom circuitry configurations.

In one method of operating the sensor system depicted in FIG. 1, a portion of the EM energy radiated by transmit line 14 is received by receive line 16, but only after the EM energy has propagated through the medium in which transmit line 14 and receive line 16 are buried. The character of the received signal depends on the properties of the medium. Thus, receive line 16 picks up some of the signal from transmit line 14, the precise amount depending on the electromagnetic properties of the medium between transmit line 14 and receive line 16. The signal in receive line 16, measured as fractional returned signal strength versus frequency, is then inverse fast Fourier transformed by signal processor 18 to produce a one-dimensional time domain signal that can be related to position down the length of transmit line 14 and receive line 16. Changes in this transformed signal indicate changes in water content or other detectable property and location of the changes.

In another method of operating the sensor system of the invention, a portion of the EM energy radiated by transmit line 14 is returned back along transmit line 14 and measured, but only after the EM energy has interacted with the medium in which transmit line 14 is buried.

In the two different methods discussed above, the measured returned signal will represent either the amount of energy transmitted through the medium or the energy returned from the medium. In either case, the return signal is a complex value having both real and imaginary terms. The complex terms are preferably used in the discrete fast Fourier transformation of the frequency data into the time domain. By the proper choice of terms, e.g., real, imaginary, magnitude, and/or phase, or the combination thereof, relative changes in the return signal can be correlated to changes in the medium properties.

In a further method of operating the sensor system of the invention, the above methods are combined such that a signal transmitted down transmit line 14 is received by receive line 16 and also is returned back along transmit line 14. This method is preferably used in order to monitor two different areas in a medium, one being immediately around the transmit line and the other more broadly distributed between the transmit and receive lines.

The above methods of operating the sensor system of the invention can include an additional data processing or interpretation step in order to generate a two-dimensional or three-dimensional profile. The one-dimensional data coming out of the sensor system in the form of a signal which is a function of distance down the cable is further processed by adding additional information about the physical layout of the cable. The one-dimensional data is thus mapped onto information about the distance and layout in the monitored physical system to generate a two-dimensional or three-dimensional profile of the detectable property. The sensor system 10 uses EM energy to detect changes in the electrical conductivity and/or dielectric properties of global or localized regions in a medium. Thus, any condition which alters the electrical complex permittivity of the medium and/or energy propagation through the medium is potentially detectable by sensor system 10. Examples of such conditions that can be monitored include changes in moisture content, chemical composition, temperature, percent solids or liquid, salinity, physical or structural integrity, ion content, and electrical conductivity.

Figure 2A:
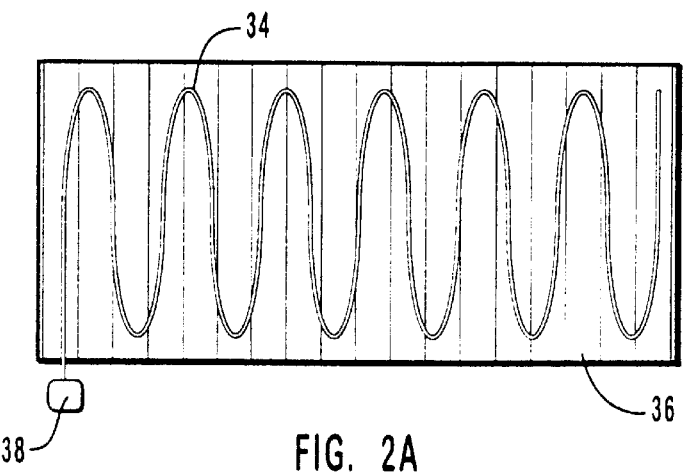
FIGS. 2A–2C are schematic diagrams of alternative application embodiments of the sensor system according to the present invention.
Figure 2B:
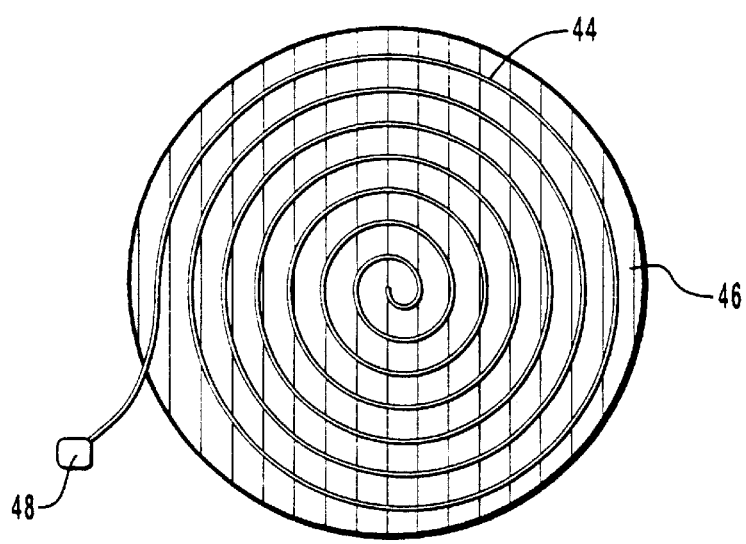
Figure 2C:
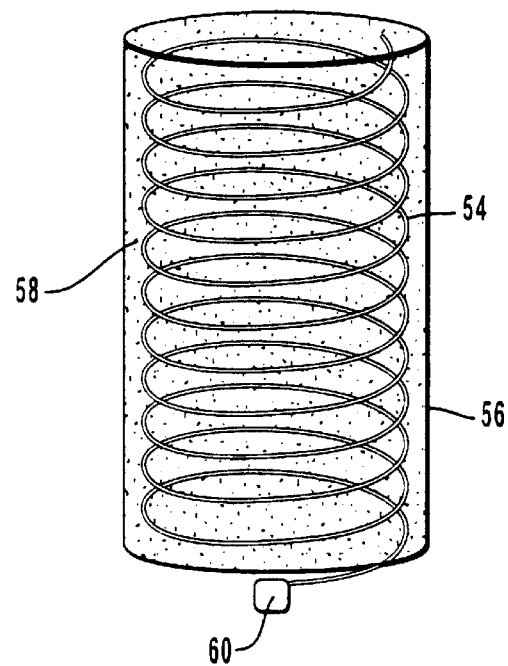

FIGS. 2A–2C depict alternative configurations for placement of the transmit/receive lines used in the sensor system of the present invention in various media. It should be understood that the electronic components as shown in FIG. 1 can be applied to the different configurations of FIGS. 2A–2C and correspond to the sensor control boxes shown in FIGS. 2A–2C. The geometries for the transmit/receive lines shown in FIGS. 2A–2C are illustrative and not limiting.

FIG. 2A shows a two-dimensional application of the sensor system of the invention in which at least one cable line 34 is installed in an S-shaped pattern across a rectangular field 36. The cable line 34 is operatively connected to a sensor control 38. FIG. 2B depicts another two-dimensional configuration in which at least one cable line 44 is installed in a spiral-shaped pattern across a circular field 46. The cable line 44 is operatively connected to a sensor control 48. In operating the two-dimensional application of the sensor system of the invention, the water content or other detectable property over the two-dimensional field is measured using the one-dimensional cable line to sample a series of locations across the field. The overall pattern of water content or other detectable property across the field can be estimated, and knowing where the cable line is physically located in two dimensions enables a two-dimensional map of water content or other detectable property to be generated for the monitored field.

A three-dimensional application of the sensor system of the invention is illustrated in FIG. 2C, in which at least one cable line 54 is helically disposed in a cylindrical structure 56 filled with a medium 58. The cable line 54 is operatively connected to a sensor control 60. In operating the three-dimensional application of the sensor system of the invention, the water content or other detectable property in the three-dimensional area is measured using the one-dimensional cable line to sample a series of locations in the area. The overall pattern of water content or other detectable property in the area can be estimated, and knowing where the cable line is physically located in three dimensions enables a three-dimensional map of water content or other detectable property to be generated for the monitored area.

The sensor system of the present invention uses the inverse fast Fourier transformed (iFFT) data directly (i.e., the signal "S") to provide information about the medium to establish a prerecorded baseline for measuring detectable properties in the medium. The sensor system uses changes in the iFFT data (i.e., $\Delta S$) to indicate changes from the prerecorded baseline, such as drying of the medium. The analyzed signal "S" indicates the spatial homogeneity of the medium, while $\Delta S$ indicates the variation in the medium over time.

For example, the sensor system of the invention can provide a profile of the water content as a function of distance along the transmission lines. The sensor system locates changes in the soil environment such as water content along the entire length of the transmission lines, by looking for changes from the baseline signal to indicate changes in water content. Materials other than water which affect the electrical conductivity and/or dielectric properties of soil, such as metals, can also be detected by the sensor system of the invention. As long as a baseline characteristic of the material is measurable, there are few limitations on the homogeneity of the material with respect to the sensor system performance.

The sensor system can be modified for different applications such as the use of very long cables or detection of only slight variations in water content or other detectable properties. Different system applications may require different data to be collected or analyzed differently to bring out other features.

In operation, the sensor system of the present invention generates a one-dimensional data output profile relating to time down the cable which corresponds to distance down the length of the cable. The term "one-dimensional" as used herein means that there is only one parameter that varies independently, which is distance down the cable. By applying the inverse fast Fourier transform to the frequency signals, a one-dimensional graph can be generated in which the peaks represent the time-related influence of the changes in detectable properties as a function of length down the cable. The one-dimensional graph can be displayed such that the x-axis is the distance down the cable and the y-axis is the water content or other detectable property.

The sensor system of the invention not only detects changes in the medium and location thereof along the transmission cable, but also can be used to provide a two-dimensional or three-dimensional profile of the spatial position of such changes. In order to create a two-dimensional interpretation of the data (e.g., water content over an agricultural field) or a three-dimensional construct (e.g., water content through a biofilter bed or a grain silo), the one-dimensional data such as water content down the length of cable can be used to create a two-dimensional or three-dimensional output for the physical system that is being measured. This can be accomplished by physically laying out the cable in a two-dimensional or three-dimensional pattern and then doing the appropriate interpolation.

If the cable is laid out in a two-dimensional pattern, measurements across a two-dimensional surface can be obtained. By installing the cable in a three-dimensional area, information in three dimensions is generated. If the cable is installed in a specific pattern, information can be generated across an area by doing interpolation between appropriate points. For example, if the cable is installed in an S-shaped pattern or spiral pattern in a field, or in a helical pattern in a biofilter bed or grain silo, a map of a two-dimensional or three-dimensional area can be created by doing the appropriate interpolation.

A two-dimensional or three-dimensional profile requires a predetermined two-dimensional or three-dimensional map of the layout of the sensor system in the medium. With this information, position data along the sensor system may be translated to a two-dimensional or three-dimensional map of changes and disturbances within the medium. The mapping of a one-dimensional signal from a cable occupying a two-dimensional or three-dimensional space can be accomplished by standard mathematical operations. Alternatively, multiple sensor cables can be distributed in an interweaved one, two or three-dimensional pattern and their separately generated signals combined to produce a one, two or three dimensional profile of the medium.

Alternatively, the sensor system of the invention may be combined with a global positioning system or other positioning system to generate a map of the medium.

In operating the sensor system of the invention to measure water content or other detectable properties in a medium, a swept or stepped frequency source of time-varying EM energy is supplied to the transmission line, and EM energy enters and propagates along the transmission line. Alternatively, a pulse of EM energy can be input into the transmission line since the pulse will contain energy at all frequencies. In principle, any waveform of input energy can be used as long as the energy content at the various frequencies needed for the analysis are either known from the way the signal was constructed or can be measured as the signal is generated. Since the EM energy is conducted along the transmission line as opposed to the medium itself, the sensor system can be used in mediums such as soils which have a high loss factor to EM energy.

By converting the measured transmission coefficient data from the frequency domain to the time domain, the location of disturbances from a prerecorded baseline of the measured transmission coefficient along the transmit line may be determined. After calibration, the time domain signal provides information on how far along the length of the transmission line the changes in the medium occurred. The frequency bandwidth of the transmitted signal will determine the range resolution and therefore the discrimination ability between independent anomalies in the medium. Range resolution of centimeters may be achieved by sweeping the signal frequency up to several gigahertz. Therefore, by adjusting the signal bandwidth, the sensor system may be adapted to different conditions and applications.

An inverse fast Fourier transform is performed by the signal processor to locate changes in the medium such as soil or other environmental changes along the entire length of the sensor system, as opposed to only point or local volume-averaged measurements in prior devices. A Fourier transform is a mathematical operation that can be used to convert a time-domain signal into the frequency domain. A discrete Fourier transform is used when there is a finite number of points rather than a continuous function to be transformed. The inverse fast Fourier transform or inverse discrete fast Fourier transform permit rapid computation of the inverse Fourier transform or inverse discrete Fourier transform of an electrical signal, thereby representing the signal in the time domain.

The fast Fourier transform is a computational technique employing the Cooley-Tukey algorithm to reduce the number of mathematical operations. The Cooley-Tukey algorithm is a well known algorithm and is set forth in *Perry's Chemical Engineers' Handbook* 2–73 (6th ed. 1984), which is incorporated herein by reference. Algorithms for carrying out the Fourier transforms are set forth in Ronald N. Bracewell, *Fourier Transform and Its Applications* (2nd ed. 1986), which is incorporated herein by reference. In a preferred technique, the sensor system of the invention uses a limited number of transmitted frequencies that are chosen to provide the desired resolution and time span, with an inverse discrete fast Fourier transform being utilized. The procedures for properly selecting these frequencies are known to those skilled in the art.

Alternative software and signal analysis schemes can also be used to convert the measured frequency data into the time domain. For example, an alternative signal processing method such as the Chirp-Z transform can be used in the present invention in place of the inverse fast Fourier transform. Various windowing methods can also be used in order to eliminate the effect of internal signal reflections.

The sensor system of the invention is relatively inexpensive and easily installed in an area to be monitored. The sensor system is quite different from prior devices in that the sensor system produces a profile of liquid phase water content or other dielectric influences as a function of distance down the measuring transmission line, rather than just a point measurement.

There are many possible applications for which the sensor system of the present invention can be employed. The water profile data provided by the sensor system of the invention is useful in a variety of areas such as agriculture, horticulture, biofiltration of industrial offgases, and in detecting and locating leaks in landfill areas or drum storage facilities including monitoring buried tanks for leaks of water or other liquids at buried waste sites. Thus, the present invention can be used in environmental cleanup activities.

In agriculture and in horticulture, the water profile data produced by the sensor system can be used to monitor plant growth and in determining local irrigation requirements including precision irrigation of field crops. For example, the cables of the sensor system can be buried in a spiral pattern to cover an entire crop field. In addition, the sensor system can be used in determining water requirements of specific high value trees in an orchard or plants in greenhouses or nurseries to control watering cycles by laying the cables out along lines of trees or down rows of plants. Alternatively, the sensor system can be used in monitoring the moisture content of agricultural products in bulk storage, such as monitoring of grain and potato storage facilities. Further, the sensor system can be used in monitoring the kiln drying of wood.

In industrial biofiltration systems, the operational need for biofilter water measurement is quite strong. The sensor system of the invention can measure any relative changes in water content in a filter bed. Thus, the water profile data provided by the sensor system can indicate improper watering of the biofilter bed or faulty flow patterns in the bed causing locally high or low amounts of reaction.

The water profile data can also be used to track water infiltration into the ground during rainstorms or as part of soil characterization studies. In addition, water profile data can be used to provide continuous monitoring of water table depths in wells, or monitoring in a well bore in which water infiltration tests are done. The water profile data produced by the sensor system can also be used in monitoring composting operations, and in maintaining lawns or golf course greens.

The sensor system of the invention can be configured to move over a material to be detected, or the monitored material can be moved relative to a fixed sensor. For example, the water content of rolling webs of paper at a papermill can be monitored by providing on-line, non-contact, full-width measurement of the moisture content of the moving web of paper in relation to a fixed sensor cable. In addition, the water content of fried or baked foods on a conveyor belt can be monitored by a fixed sensor cable according to the present invention. If the sensor is moved relative to the material to be detected, a device for determining and recording the location and/or orientation of the sensor as the data is recorded can usefully be added to the system. For instance, if a sensor oriented in the north-south direction is moved horizontally in the east-west direction across a field, a device for recording the east-west location would allow creation of a two dimensional map of water content in the soil in the field. In an expanded version of this idea, if the sensor is attached to a tractor which drives an arbitrary pattern over the field, recording both the position of the tractor (for example, using a positioning system such as a global positioning system (GPS) locator) and its orientation (for example, using a compass) would allow reconstruction of the sensor's exact location and orientation when the data was collected. This in turn would allow construction of a map of the properties of the entire surface over which the tractor was driven while data was being collected.

Another application of the sensor system of the invention includes the detection of leaks from underground storage tanks for hydrocarbons such as motor fuels. In addition, other applications include liquid level sensing in chemical processing, on-line monitoring of polymerization of plastics, and curing of concrete materials. The sensor system can also be used as a liquid level detector in tanks having foams or highly aerated liquids which interfere with many other detection systems.

In a different application, which looks for a "spike" signal rather than a broad profile, the sensor system can be adapted for use as a security device in an area to detect a person (mainly made of water) who walks over the area. For example, in a detection environment such as a security perimeter, the present invention can be used to determine where a person is in relation to the length of the sensor cable. The sensor system could also be adapted to detect metals or objects made therefrom such as vehicles. The sensor system can be configured to detect and locate persons or vehicles crossing or walking along a security perimeter, even if done so in two or more places simultaneously.

A related application would be to detect water intrusion into a nominally dry system, such as monitoring water infiltration into cracked concrete structures. For instance, water penetrating a crack in a concrete beam, in which one of the present sensing cables had been placed as the beam was cast, could be monitored. In addition, the sensor system can be potentially adapted to detect ice on runways.

Since the sensor system can detect location along the cable at a period of time, the sensor system can also be used to track the speed of movement of both vehicles and people if they move along the length of the sensing cable.

The specific embodiments discussed above should not be considered as limitations on the scope of the invention, but rather as exemplifications of preferred embodiments since many variations are possible.

The following examples are given to illustrate the present invention and should not be viewed as limiting the scope of the invention.

EXAMPLE 1

A laboratory experiment was performed in order to demonstrate the operation of the present invention. A sensor system was constructed including two slotted coaxial cables attached to a microwave generator and a laboratory network analyzer. The two slotted coaxial cables were laid out parallel to each other on a floor and then buried with semi-dry compost. When small perturbations in the compost moisture were made at different locations along the cables, the transmission coefficient resulting from the coupled energy between the two cables showed good sensitivity to the changes. The transmission coefficient was measured as a function of frequency and converted to the time domain. In the time domain, when the perturbations in the soil moisture were made at different locations along the cables, the perturbations and their location along the cables were detectable.

EXAMPLE 2

A sensor system was constructed including two slotted coaxial cables attached to a microwave generator and a laboratory network analyzer. The cables were buried in a twenty foot long trough of compost material simulating a biofilter application. When operated, the sensor system readily detected changes in water content of 0.05 g water/g soil. Changes on the order of 0.1 g/g are significant in biofilters, so good sensitivity was shown.

EXAMPLE 3

A sensor system was constructed comprising slotted coaxial cable lines 10 feet long attached to a microwave generator and a laboratory network analyzer. The slotted cable lines included a transmit line and a receive line that were one inch apart, and each line terminated with 50 ohms, which was the same impedance as the cable lines. The slotted cable lines were laid in a plastic tray and immersed in compost which had been air dried in room air and at room temperature for over two weeks. At 96.5 inches down the slotted cable lines and away from the network analyzer, an approximate 15 inch section of compost was removed and mixed with enough water to make a 15% by weight water content. This water/compost mixture was then added back to the section of compost where originally removed. Reference data at the starting time was then taken, with subsequent data taken at time periods of 18 hours, 42 hours, and 60 hours after the reference data. The boundaries of the region of compost with added water were softened by a gradual mixing with the dry compost on each boundary. The signal frequency was swept from 1 MHz to 1000 MHz with 401 frequency points, and 10 dBm (10 mW) of power was applied.

Figure 3:
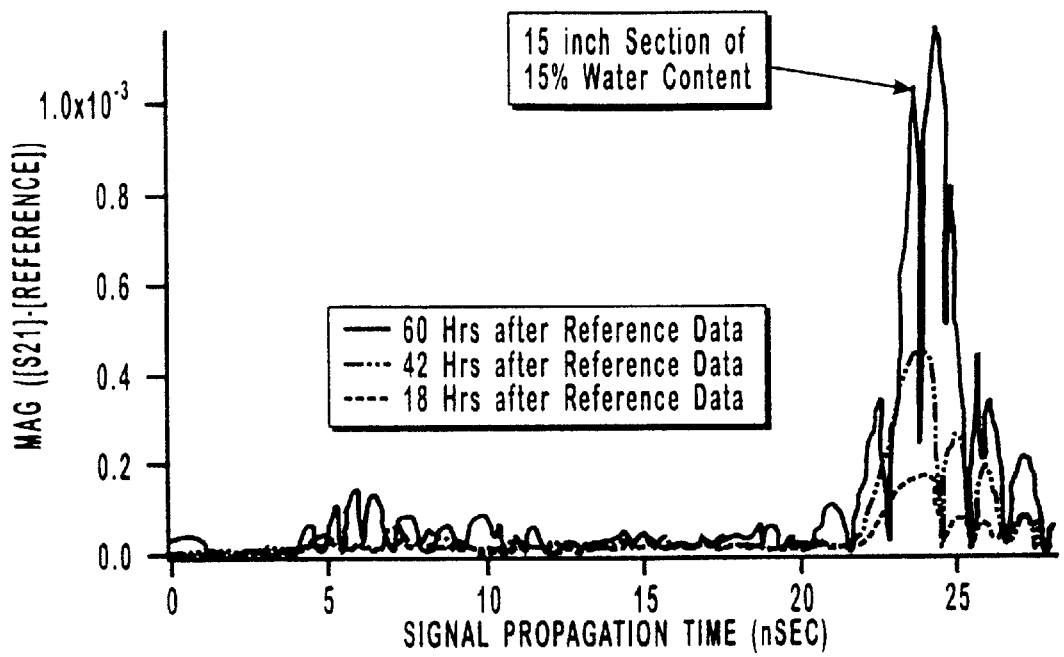
FIG. 3 is a graph depicting signal propagation time in relation to signal magnitude as measured by the sensor system of the invention in one medium.

FIG. 3 is a graph of the data collected during the above time periods depicting signal propagation time in relation to signal magnitude. The time shown is round trip time of propagation of the signal with $S_{21}$ being the measured parameter. The parameter $S_{21}$ is the signal response in the receive line versus the power in the transmit line (i.e., the ratio of signal returned vs. signal transmitted). The one-dimensional plot in the graph of FIG. 3 is the magnitude of the difference between the measured $S_{21}$ magnitude at the three different time periods and that measured at the starting reference time. The graph shows the changes in properties of the compost as the wet part was dried over the measured time periods of 18 hours, 42 hours, and 60 hours.

EXAMPLE 4

A sensor system was constructed as described above in Example 3. The slotted cable lines were laid in a plastic tray and immersed in compost which had been air dried in room air and at room temperature for over two weeks. At 96.5 inches down the slotted cable lines and away from the network analyzer, an approximate 15 inch section of compost was removed and mixed with enough water to make a 6% by weight water content. This water/compost mixture was then added back to the section of compost where originally removed. Reference data at the starting time was then taken, with subsequent data taken at time periods of 4 hours, 8 hours, and 16 hours after the reference data. The signal frequency was swept from 1 MHz to 1000 MHz with 401 frequency points, and 10 dBm (10 mW) of power was applied.

Figure 4:
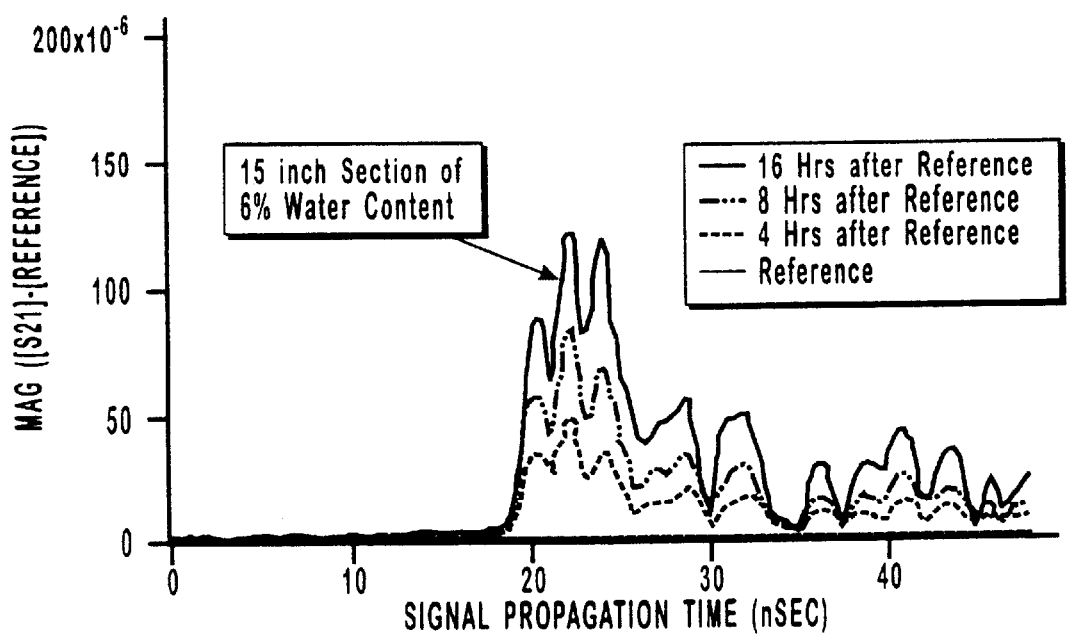
FIG. 4 is a graph depicting signal propagation time in relation to signal magnitude as measured by the sensor system of the invention in another medium.

FIG. 4 is a graph of the data collected during the above time periods depicting signal propagation time in relation to signal magnitude. The time shown is round trip time of propagation of the signal with $S_{21}$ being the measured parameter. The one-dimensional plot in the graph of FIG. 4 is the magnitude of the difference between the measured $S_{21}$ magnitude at the three different time periods and that measured at the starting reference time. The graph shows the changes in properties of the compost as the wet part was dried over the measured time periods of 4 hours, 8 hours, and 16 hours.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A system for monitoring detectable properties in a medium, comprising:
   a. means for generating and transmitting an electromagnetic signal;
   b. signal leaking transmission line operatively connected to the generating means; and
   c. means for processing and analyzing data received from the transmission line;
      wherein the electromagnetic signal is transmitted along the transmission line and is returned and processed to generate a one-dimensional profile that is a function of a detectable property of a medium being monitored.

2. The system of claim 1, wherein the generating means is a signal generator.

3. The system of claim 2, wherein the signal generator comprises a microwave sweep oscillator.

4. The system of claim 1, wherein the transmission line is a slotted coaxial cable.

5. The system of claim 1, wherein the processing means includes a digital signal processor.

6. The system of claim 1, further comprising a power coupling device operatively connected to the transmission line.

7. The system of claim 6, further comprising a signal detection device operatively connected to the power coupling device.

8. The system of claim 7, wherein the processing means is operatively connected to the signal detection device.

9. The system of claim 1, further comprising an output device for displaying the profile generated by the processing means.

10. The system of claim 1, wherein the processing means generates the one-dimensional profile of the detectable property of the medium by using an inverse fast Fourier transform algorithm to convert data from a frequency domain to a time domain.

11. The system of claim 10, wherein the processing means further comprises a data processor for mapping the one-dimensional profile onto a physical system in order to generate a two-dimensional profile or a three-dimensional profile.

12. The system of claim 11, wherein the transmission line has a two-dimensional configuration.

13. The system of claim 12, wherein the two-dimensional configuration is an S-shaped pattern or a spiral pattern.

14. The system of claim 11, wherein the transmission line has a three-dimensional configuration.

15. The system of claim 14, wherein the three-dimensional configuration is a helical pattern.

16. The system of claim 1, further comprising a receive line in proximity to the transmission line and operatively connected to the processing means.

17. The system of claim 16, wherein the transmission line and the receive line are substantially parallel to one another.

18. A system for monitoring water content or other detectable properties in a medium, comprising:
   a. a signal generator;
   b. a signal leaking transmission line operatively connected to the signal generator;
   c. a signal leaking receive line in proximity to the transmission line; and
   d. a signal processor for processing and analyzing data received from the transmission line and/or the receive line.

19. The system of claim 18, additionally comprising an output device for displaying a profile generated by the signal processor.

20. The system of claim 18, wherein the signal generator comprises a microwave sweep oscillator.

21. The system of claim 18, wherein the transmission line is a slotted coaxial cable.

22. The system of claim 18, wherein the receive line is a slotted coaxial cable.

23. The system of claim 18, further comprising a power coupling device operatively connected to the transmission line and the receive line.

24. The system of claim 22, further comprising a signal detection device operatively connected to the power coupling device.

25. The system of claim 23, wherein the signal processor includes a digital signal processor operatively connected to the signal detection device.

26. The system of claim 18, wherein the signal processor generates the one-dimensional profile of the detectable property of the medium by using an inverse fast Fourier transform algorithm to convert data from a frequency domain to a time domain.

27. The system of claim 18, further comprising a data processor for mapping the one-dimensional profile onto a physical system in order to generate a two-dimensional profile or a three-dimensional profile.

28. The system of claim 26, wherein the transmission line and the receive line have a two-dimensional configuration.

29. The system of claim 27, wherein the two-dimensional configuration is an S-shaped pattern or a spiral pattern.

30. The system of claim 26, wherein the transmission line and the receive line have a three-dimensional configuration.

31. The system of claim 29, wherein the three-dimensional configuration is a helical pattern.

32. The system of claim 18, wherein the transmission line and the receive line are substantially parallel to one another.

33. A method for monitoring detectable properties in a medium, comprising the steps of:
   a. placing a sensor system proximate to a medium to be monitored;
   b. transmitting an electromagnetic signal from a signal generator along a signal leaking transmission line of the sensor system;
   c. returning the transmitted electromagnetic signal back along the transmission line;
   d. processing the returned signal to generate a one-dimensional profile that is a function of a detectable property of the medium; and
   e. displaying a selected amount of the profile on an output device of the sensor system.

34. The method of claim 33, wherein the electromagnetic signal is transmitted as a swept or stepped frequency signal of electromagnetic energy.

35. The method of claim 33, wherein the electromagnetic signal is transmitted as a pulse of electromagnetic energy.

36. The method of claim 33, wherein the electromagnetic signal transmitted has a frequency from the audio to the microwave range.

37. The method of claim 33, further comprising the step of transmitting a reference signal along the transmission line to establish a prerecorded baseline for measuring changes in detectable properties of the medium.

38. The method of claim 37, wherein the sensor system uses changes in subsequently transmitted electromagnetic signals from the prerecorded baseline to measure changes in the detectable properties of the medium.

39. The method of claim 33, wherein the one-dimensional profile includes information related to changes in the detectable properties of the medium selected from the group consisting of moisture content, chemical composition, temperature, percent solids or liquid, salinity, physical integrity, and structural integrity.

40. The method of claim 33, wherein the processing step generates the one-dimensional profile of the detectable property of the medium by using an inverse fast Fourier transform algorithm to convert data from a frequency domain to a time domain.

41. The method of claim 33, further comprising the step of mapping the one-dimensional profile onto a physical system in order to generate a two-dimensional profile or a three-dimensional profile.

42. The method of claim 33, further comprising the step of burying the transmission line in the medium to be monitored.

43. The method of claim 42, wherein the transmission line is buried in the medium in a two-dimensional configuration.

44. The method of claim 43, wherein the two-dimensional configuration forms an S-shaped pattern or a spiral pattern.

45. The method of claim 42, wherein the transmission line is buried in the medium in a three-dimensional configuration.

46. The method of claim 45, wherein the three-dimensional configuration forms a helical pattern.

47. The method of claim 33, further comprising the step of moving the transmission line relative to the medium to be monitored while transmitting the electromagnetic signal.

48. The method of claim 47, further comprising the step of operating a map of the area being monitored by means of integration of input from a positioning system.

49. The method of claim 33, wherein the medium is a compost material in a biofilter system or a composting operation.

50. The method of claim 33, wherein the medium is soil in an area selected from the group consisting of a crop field, an orchard, a greenhouse, a nursery, a lawn, and a security perimeter.

51. The method of claim 33, wherein the medium is soil at a buried waste site or a landfill area.

52. A method for monitoring water content or other detectable properties in a medium, comprising the steps of:
   a. placing a sensor system proximate to a medium to be monitored;
   b. transmitting an electromagnetic signal from a signal generator along a signal leaking transmission line of the sensor system;
   c. returning the transmitted electromagnetic signal back along the transmission line and/or into a receive line in proximity to the transmission line; and d. processing the returned signal to generate a one-dimensional profile that is a function of a detectable property of the medium.

53. The method of claim 52, additionally comprising the step of displaying a select amount of the profile on an output device of the sensor system.

54. The method of claim 52, wherein the electromagnetic signal is transmitted as a swept or stepped frequency signal of electromagnetic energy.

55. The method of claim 52, wherein the electromagnetic signal is transmitted as a pulse of electromagnetic energy.

56. The method of claim 52, wherein the electromagnetic signal transmitted has a frequency from the audio to the microwave range.

57. The method of claim 52, further comprising the step of transmitting a reference signal along the transmission line to establish a prerecorded baseline for measuring detectable properties of the medium.

58. The method of claim 57, wherein the sensor system uses changes in subsequently transmitted electromagnetic signals from the prerecorded baseline to measure changes in the detectable properties of the medium.

59. The method of claim 52, wherein the one-dimensional profile includes information related to changes in the detectable properties of the medium selected from the group consisting of moisture content, chemical composition, temperature, percent solids or liquid, salinity, physical integrity, and structural integrity.

60. The method of claim 52, wherein the processing step generates the one-dimensional profile of the detectable property of the medium by using an inverse fast Fourier transform algorithm to convert data from a frequency domain to a time domain.

61. The method of claim 52, further comprising the step of mapping the one-dimensional profile onto a physical system in order to generate a two-dimensional profile or a three-dimensional profile.

62. The method of claim 52, further comprising the step of burying the transmission line and the receive line in the medium to be monitored.

63. The method of claim 62, wherein the transmission line and the receive line are buried in the medium in a two-dimensional configuration.

64. The method of claim 63, wherein the two-dimensional configuration forms an S-shaped pattern or a spiral pattern.

65. The method of claim 62, wherein the transmission line and the receive line are buried in the medium in a three-dimensional configuration.

66. The method of claim 65, wherein the three-dimensional configuration forms a helical pattern.

67. The method of claim 52, further comprising the step of moving the transmission line and the receive line relative to the medium to be monitored while transmitting the electromagnetic signal.

68. The method of claim 67, further comprising the step of generating a moisture map of the area being monitored by obtaining input from a positioning system for the sensor system.

69. The method of claim 52, wherein the medium is a compost material in a biofilter system or a composting operation.

70. The method of claim 52, wherein the medium is soil in an area selected from the group consisting of a crop field, an orchard, a greenhouse, a nursery, a lawn, and a security perimeter.

71. The method of claim 52, wherein the medium is soil at a buried waste site or a landfill area.

* * * * *